United States Patent [19]

De Godoy Moreira

[11] Patent Number: 5,350,365
[45] Date of Patent: Sep. 27, 1994

[54] SURGICAL INSTRUMENT FOR INJECTING/REMOVING NON-SOLID SUBSTANCES

[76] Inventor: Roberto De Godoy Moreira, Rua Sao Salvador, 99, Sao Paulo, SP, Brazil

[21] Appl. No.: 101,460

[22] Filed: Aug. 2, 1993

[30] Foreign Application Priority Data

Nov. 16, 1992 [BR] Brazil .................. PI 9204536

[51] Int. Cl.$^5$ .................. A61M 5/00; A61M 5/315
[52] U.S. Cl. .................. 604/187; 604/209; 604/220; 604/223; 604/227
[58] Field of Search .................. 604/60, 186, 207–210, 604/220, 223, 227, 228, 246, 233, 187; 222/324–327

[56] References Cited

U.S. PATENT DOCUMENTS

| | | | |
|---|---|---|---|
| 530,187 | 12/1894 | Laskey | 604/223 |
| 2,074,401 | 3/1937 | Kauzal | 604/208 |
| 3,110,310 | 11/1963 | Cislak | 604/209 |
| 3,905,365 | 9/1975 | Colombo | 604/223 |
| 4,014,331 | 3/1977 | Head | 604/223 |
| 4,738,664 | 4/1988 | Prindle | 604/228 |
| 4,826,483 | 5/1989 | Molner, IV | 604/210 |
| 5,136,507 | 8/1992 | Haber et al. | 604/223 |

FOREIGN PATENT DOCUMENTS

| | | | |
|---|---|---|---|
| 0603401 | 9/1934 | Fed. Rep. of Germany | 604/209 |
| 1186571 | 8/1959 | France | 604/207 |

*Primary Examiner*—C. Fred Rosenbaum
*Assistant Examiner*—Frank Wilkens, III
*Attorney, Agent, or Firm*—Helfgott & Karas

[57] ABSTRACT

A surgical instrument for injecting/removing non-solid substances is diclosed. The instrument comprises a body formed from two legs (1, 2) pivotally articulated to each other at one of their ends, one of said legs (1) being provided with means (15,17) for receiving and retaining a syringe or squirt (16) while the other of said legs (2) is provided with means (20,22) for selectively retaining a plunger (19) which cooperates with said syringe or squirt, said legs being selectively pivotable between a first position wherein said plunger (19) is received within said syringe (16) and a plurality of positions wherein plunger (18) moves within syringe (16) in order to inject/remove a non-solid substance.

9 Claims, 3 Drawing Sheets

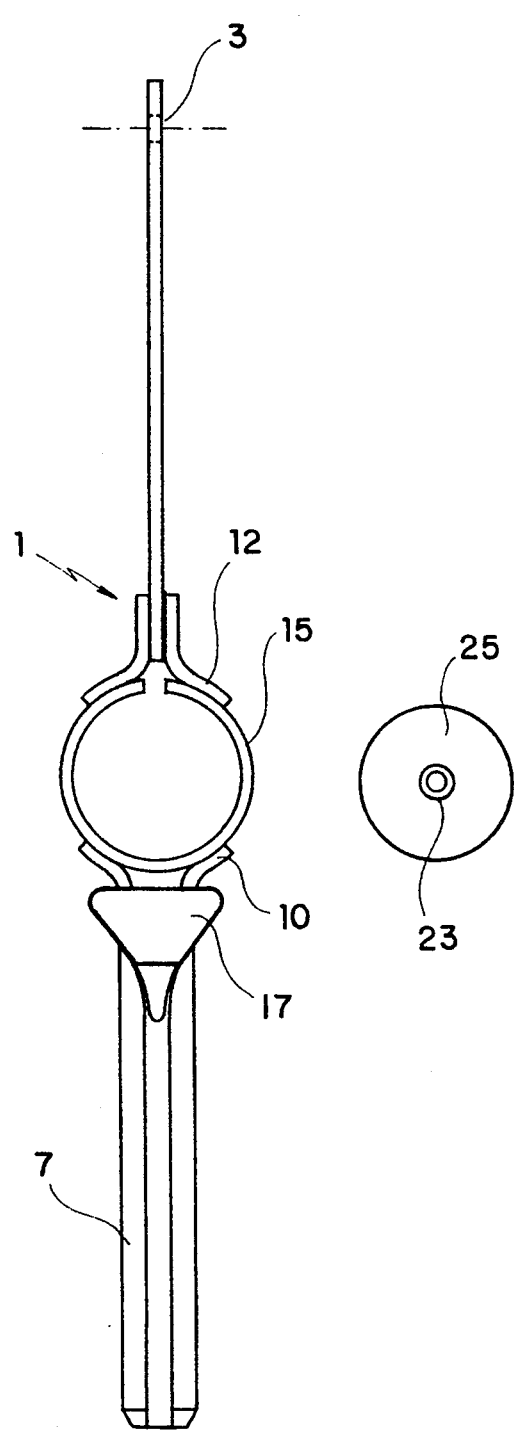
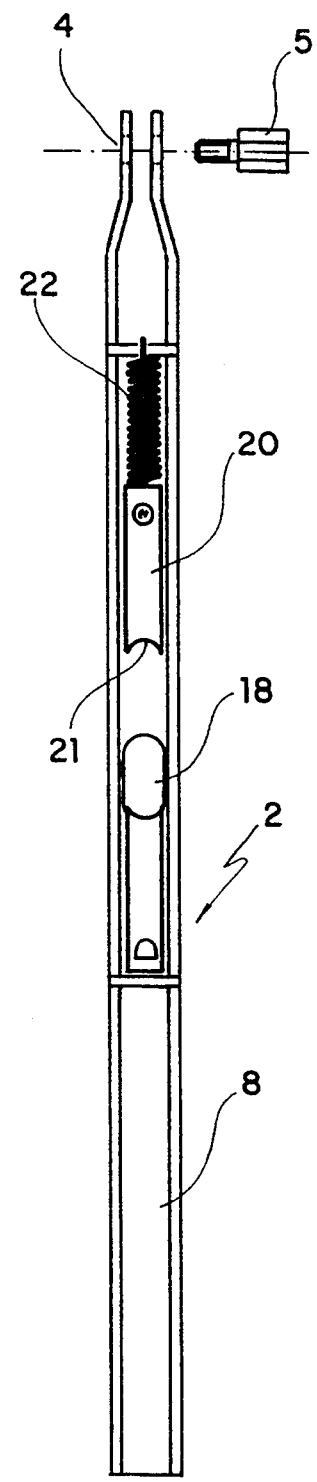
Fig. 3                    Fig. 4

SURGICAL INSTRUMENT FOR INJECTING/REMOVING NON-SOLID SUBSTANCES

BACKGROUND OF THE INVENTION

Field of the Invention

The present invention refers to surgical instruments in general, and more specifically to a new constructive arrangement provided in a surgical instrument particularly suitable for use in surgeries wherein the insertion and/or removal of non-solid substances is required.

Inserting and/or removing non-solid substances from the human body is a widely known surgical technique used by surgeons in different fields of surgery for several different purposes. Such purposes range from the injection of medicinal cements in orthopedic surgeries for speeding up the recovery of a fracture, or silicone in plastic surgeries, to the removal of fats and other liquid secretions.

As it is widely known by those skilled in such surgical arts, typically the commercially avaliable non-solid substances to be inserted into the human body are packed in the form of syringes or squirts, by means of which the product may be injected into the desired places.

The greatest problem of using said non-solid substances however, lies in the injection application of the product.

Actually, the characteristics of some of said products, such as high density and low fluidity besides the size and weight of these syringes and squirts, prevent them from being used as conventional injection syringes.

Therefore, generally, the injection of such non-solid substances involves the use of special surgical instruments commonly known as pistols or guns.

Typically, these guns comprise a housing for receiving the syringe or squirt containing non-solid substances and an alternative triggering system which actuates a plunger in order to force the non-solid substances to leave the syringes or squirts and penetrate into the human body.

However, the use of such guns for injecting non-solid substances poses some problems which need to be solved so that the same may be further used.

One primary and serious drawback of such guns is directly related to the alternative triggering mechanism used for actuating the plunger that forces the non-solid substances to leave the squirt.

In effect, the use of an alternative triggering mechanism for actuating the plunger involves an intermitent movement of the plunger, that is, step by step. Therefore, as a consequence, the application of non-solid substances shall be prone to interruptions in its continuity which, besides providing an uneven application of the product, may even jeopardize the final result of the surgery in some situations.

For example, when a gun is used for injecting medicinal cement in an orthopedic surgery, the intermitent movement of the plunger allows for the formation of air bubbles within the cement being applied, which seriously jeopardize the stability of the consolidation desired.

Another drawback of these guns for injecting non-solid substances is the relatively heavy weight of the gun with the syringe or squirt mounted thereon, which makes its use difficult since any little disbalance may impair a precise application of the non-solid substance.

Additionally, since these guns are manufactured from disposable materials such as non-sterilizable plastic materials they may only be used once, which raises the cost of every surgery.

SUMMARY OF THE INVENTION

Therefore, one purpose of the present invention is to provide a surgical instrument for injecting non-solid substances which solves the above discussed problems of the presently known devices for such purpose.

Another purpose of the present invention is to provide such a surgical instrument for injecting non-solid substances which allows for a continuous and uniform application of said non-solid substances.

Still another purpose of the present invention is to provide such a surgical instrument for injecting non-solid substances which is versatile, that is, may be used with different sizes of syringes or squirts according to the needs of every surgery.

An additional purpose of the present invention is to provide such a surgical instrument for injecting non-solid substances having a light weight and easy to use so that the application of said non-solid substances in locations where they are not required may be avoided.

Still an additional purpose of the present invention is to provide such a surgical instrument for injecting non-solid substances which may be manufactured from a sterilizable material in order to allow its use in several surgeries.

Still another additional purpose of the invention is to provide such a surgical instrument which, besides injecting non-solid substances, may also remove non-solid substances from the human body.

According to the present invention, these and other purposes and advantages are achieved by the provision of a surgical instrument for injecting/removing non-solid substances into or from the human body comprising: a body having two pivotally articulated legs at one of their ends; one of said legs having means for receiving and retaining a syringe or squirt, while the other of said legs having with means for selectively retaining a plunger which cooperates with said syringe or squirt; said legs being selectively pivotable between a first position wherein said plunger is received within said syringe ou squirt and a plurality of positions wherein the plunger moves within the syringe in order to inject a substance from said syringe into a body and/or to remove a substance from a body into said syringe.

BRIEF DESCRIPTION OF THE DRAWINGS

The present invention shall be described in greater details hereinafter with reference to its presently preferred embodiment shown in the accompanying drawings, wherein:

FIGS. 3 and 4 are plan views of the surgical instrument legs.

DESCRIPTION OF THE PREFERRED EMBODIMENT

Figure 1:
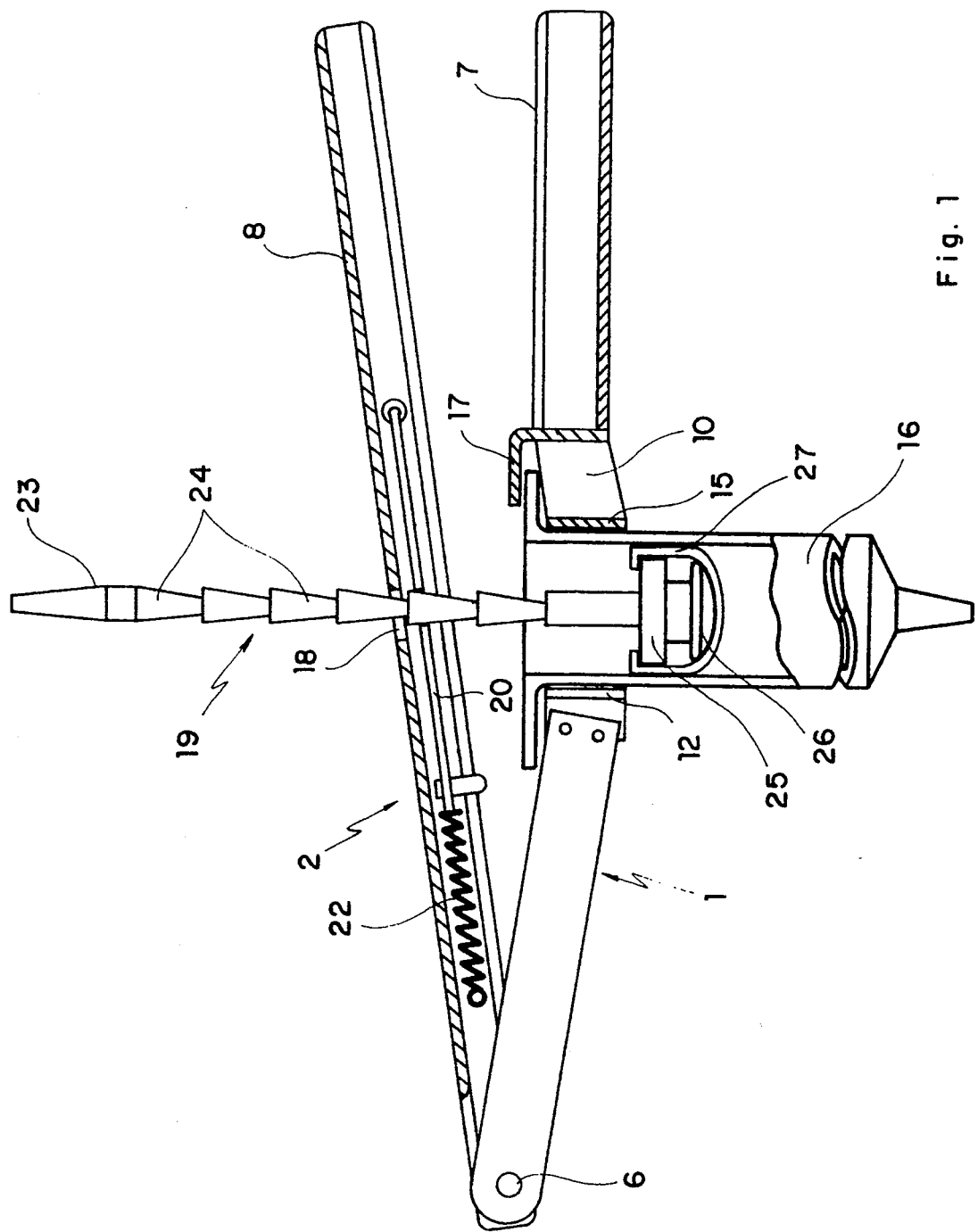
FIG. 1 is a side elevational view of the surgical instrument according to the present invention, showing the plunger partially inserted into a syringe.
Figure 2:
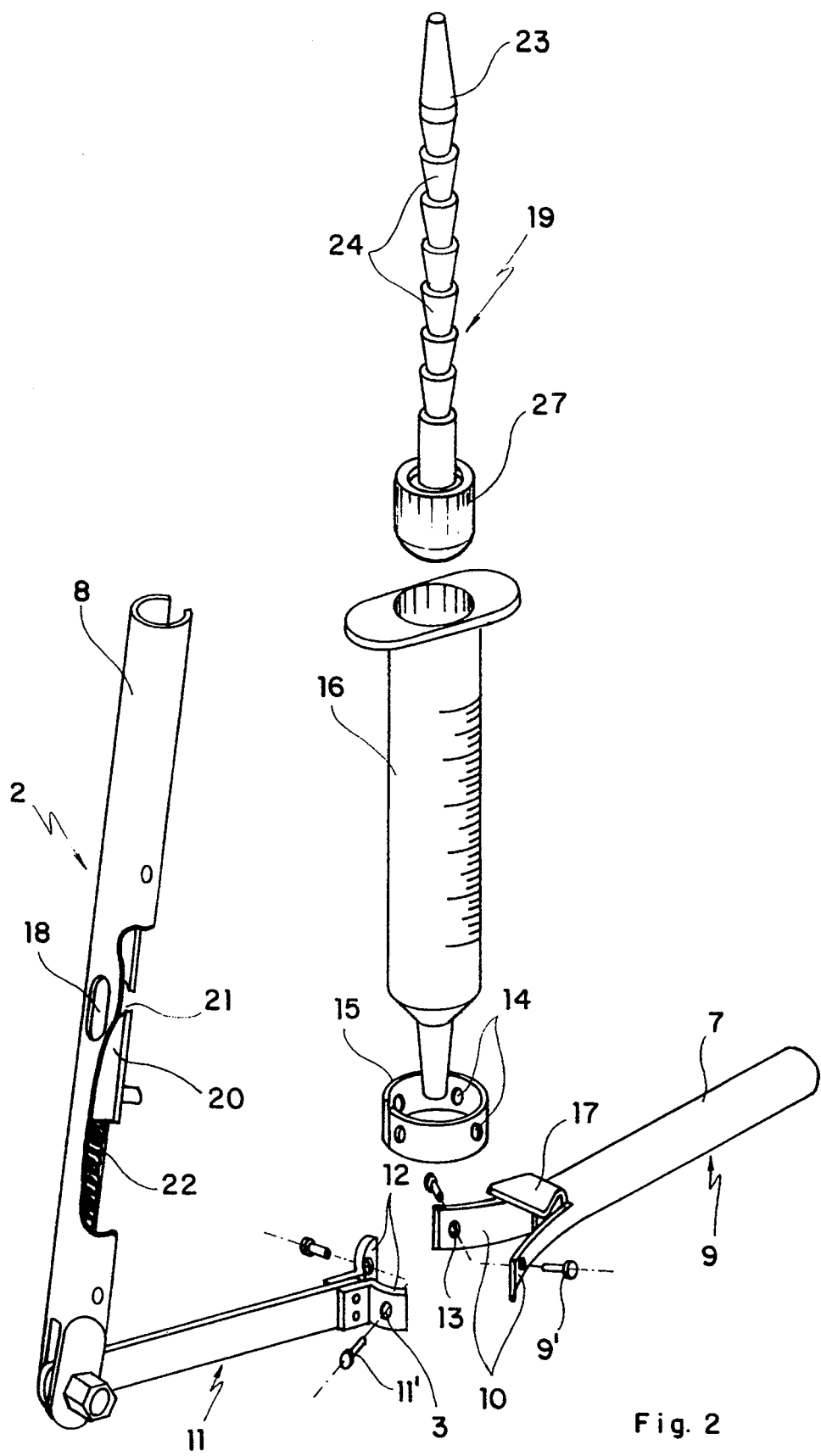
FIG. 2 is an exploded perspective view of the surgical instrument according to FIG. 1.

With particular reference to the drawings, a surgical instrument for injecting/removing a non-solid substance into/from a body, particularly a human body, according to the present invention is shown in FIG. 1 as comprising, basically, a body having two legs 1, 2 pivotally articulated to each other at one of its ends where two trespassing bores 3, 4 for receiving a pivot axis 5 fastened thereto by a nut 6 or the like are formed.

Each of said legs 1, 2 is manufactured from a suitable metallic material prone to be sterilized, having a round portion at its free end in order to define handle portions 7,8.

Additionally, one of said legs is provided with means for receiving and retaining a syringe or squirt, which means will be described hereinafter in greater detail.

Leg 1 is segmented along its length so that a first lower half 9 provided with tabs 10 and an upper half 11 provided with tabs 12 are defined therein. Transpassing bores 13 are formed in said tabs 10,12 whose purpose is to cooperate with corresponding bores 14 formed in a receiving ring 15 the diameter of which varies according to the diameter of the syringe or squirt 16 to be used. A tab 17 in the above-mentioned lower half cooperates with similar tabs formed in the syringes or squirts for holding same into position.

This constructive arrangement allows the surgical instrument according to the present invention to receive and accommodate syringes or squirts having different diameters, depending on the material to be used in the surgery.

The second one 2 of the above-mentioned pair of legs 1, 2 is provided with a transpassing bore 18 in a position along its length approximately corresponding to the geometric center of a syringe or squirt 16 placed in the receiving ring 15 of the first leg 1, for receiving and retaining a plunger 19 cooperating with the syringe when it is in position.

For this purpose, second leg 2 is provided with a guillotine-type fastening system comprising a blade 20 having a transpassing bore 21 therein, said blade being slidable between a first position wherein said bore 21 is aligned with bore 18 in leg 2 and a second position wherein said bores 18, 21 are not aligned. A spring 22 is used for biasing said blade to said second misaligned position, in order to retain said plunger 18.

In order to cooperate with each different size of syringe or squirt, plunger 19 is provided with a plunger rod 23 having a plurality of peripheral grooves 24 along its length and a threaded end 25 where a headstock 26 or the like is received.

The peripherical grooves 24 serve to define the multiple positions wherein plunger 19 may be fastened to the above-described guillotine-type fastening system in leg 2. Said grooves may have a straight profile so that the surgical instrument according to the present invention may be used not only for injecting non-solid substances, but also for removing body fluids.

Additionally, said grooves may be formed which such a profile that intermediate portions having a conical profile may be defined, which would allow for a movement of the plunger rod through the surgical instrument leg hole without the need to unlock the fastening system thereof.

Headstock 26, which is threaded on the right end of plunger 19, serves as a support for a plurality of rubber covers 27 or the like, each of which corresponds to a different dimension or diameter of the syringe or squirt, therefore allowing the utilization of the surgical instrument provided with syringes or squirts having different dimensions.

The operation of the surgical instrument according to the present invention is simple and shall be briefly described herebelow with respect to its utilization for injecting a non-solid substance.

After the component parts are sterilized, a receiving ring 15 with a diameter corresponding to that of the syringe or squirt 16 to be used is respectively attached to tabs 10, 12 at lower 9 and upper 11 halves of first leg 1, and a corresponding rubber cover 27 or the like is mounted on headstock 26 which is threaded on end 25 of plunger 19.

Syringe or squirt 16 is then inserted into receiving ring 15 and rotated by 90° whereby its tab is engaged under tab 17 so that the syringe is retained into position. Next, plunger 19 is retained in leg 2 opposite to the surgical instrument by engaging said blade 20 in one of the peripherical grooves 24 on the plunger rod 19.

After the surgical instrument has been assembled, the selective pivoting of said legs 1, 2 causes plunger 19 to move within syringe or squirt 16, whereby the non-solid substance is injected into the pacient.

This constructive arrangement of the surgical instrument allows for an uniform application of non-solid substance without interrupting the continuity, which is one of the main purposes of the present invention. Additionally, said constructive arrangement provides the surgical instrument according to the present invention with a great versatility, which instrument may then be used with different sizes of syringes or squirts in accordance with the needs of every surgery.

Also, in view of the fact that the surgical instrument according to the present invention has a light weight and easy to use, the application of said non-solid substances in locations where they are not required is prevented, therefore increasing the safety of application.

The present invention having been described and ilustrated, it shall be understood that several modifications and variations may be made thereto, since said modifications and variations do not depart from the spirit and scope of the invention as defined in the attached claims.

I claim:

1. A surgical instrument for injecting/removing non-solid substances from a body, particularly a human body, comprising first and second legs (1, 2) pivotally connected to each other at a respective first end of each, said first leg having means (15, 17) for receiving and retaining a syringe (16), and said second leg having means (18, 22) for selectively retaining a plunger (19) in cooperation with said syringe, said first and second legs being selectively pivotable between a first position wherein said plunger (19) is received within said syringe (16) and a plurality of second positions wherein said plunger (18) moves within said syringe (16) in order to inject/remove a non-solid substance, wherein said means for receiving and retaining includes a receiving ring having bores and said first leg has an upper half and a lower half, each of said upper and lower halves having first tabs with through bores extending therethrough wherein said receiving ring is attached to said first tabs of both said upper and lower halves through cooperation between said bores and through bores.

2. A surgical instrument according to claim 1, wherein said first and second legs (1, 2) each have a first transpassing bore (3, 4) at their respective first ends and are pivotally fastened thereto by a nut (6) extending through the transpassing bore in both the respective first and second legs.

3. A surgical instrument according to claim 1, wherein said receiving ring (15) includes means for adapting a diameter of the receiving ring to hold syringes having different dimensions.

4. A surgical instrument according to claim 1, additionally comprising a second tab (17) on said lower half (9) of said first leg cooperating with third tabs formed on syringes (16) for holding said syringes in position.

5. A surgical instrument according to claim 1, wherein said means for selectively retaining a plunger comprises a second transpassing bore (18); a guillotine-type fastening system comprising a blade (20) provided with a through hole (21), said blade being slidable between a first position wherein said through hole (21) is aligned with said second transpassing bore (18) and a second position wherein said through hole and second transpassing bore are not aligned; and a spring (22) for forcing said blade (20) into said second position.

6. A surgical instrument according to claim 1, wherein said means for selectively retaining said plunger are positioned on said second leg (2) for receiving said plunger (19) in a position approximately corresponding to the geometric center of said syringe (16).

7. A surgical instrument according to claim 1, wherein said plunger (19) comprises a plunger rod (23) provided with a plurality of peripheral grooves (24) along its length; a threaded end (25); and a headstock received on said threaded end.

8. A surgical instrument according to claim 7, further comprising a plurality of rubber covers wherein said headstock (26) is positioned at a front end of said plunger (19) and serves as a support for one of a plurality of rubber covers (27) each of said plurality of rubber covers corresponding to a diameter of a respective syringe (16).

9. A surgical instrument according to claim 1, wherein said instrument is formed from a suitable sterilization metallic material.

\* \* \* \* \*